United States Patent [19]

Meinert

[11] Patent Number: 5,441,733
[45] Date of Patent: Aug. 15, 1995

[54] TREATMENT AGENT FOR OPHTHALMOLOGY AND USE THEREOF

[75] Inventor: Hasso Meinert, Neu-Ulm, Germany

[73] Assignee: PharmPur GmbH, Augsburg, Germany

[21] Appl. No.: 4,005

[22] Filed: Jan. 15, 1993

[51] Int. Cl.⁶ ...................... A61K 31/74; A61K 31/03
[52] U.S. Cl. .................. 424/78.04; 514/746; 514/912
[58] Field of Search ............... 514/754, 772, 912, 746; 424/78.04

[56] References Cited

FOREIGN PATENT DOCUMENTS

| | | |
|---|---|---|
| 0089232 | 9/1983 | European Pat. Off. . |
| 0089815 | 9/1983 | European Pat. Off. . |
| 0112658 | 4/1984 | European Pat. Off. . |
| 0381986 | 8/1990 | European Pat. Off. . |
| 0493677 | 7/1992 | European Pat. Off. . |
| 0496299 | 7/1992 | European Pat. Off. . |
| 2214674 | 8/1974 | France . |
| 2623525 | 5/1989 | France . |
| 889282 | 2/1962 | United Kingdom . |

OTHER PUBLICATIONS

The Merck Index, 11th Edition (1989) p. 657.
J. Chem. Soc. (C), 1967, pp. 1450–1454.
Chemical Abstracts, vol. 83, 1975, p. 758.
Chemical Abstracts, vol. 87, 1977, p. 26.
Chemical Abstracts, vol. 90, 1979, p. 462.
Chemical Abstracts, vol. 95, 1981, p. 634.
Chemical Abstracts, vol. 112, 1990, p. 700.

Primary Examiner—Zohteh Fay
Attorney, Agent, or Firm—Keck, Mahin & Cate

[57] ABSTRACT

A treatment agent for ophthalmology comprising a liquid perfluorinated compound (modified perfluorcarbon) of one of the types:

$R_F(CH_2)_n R_F$ with $n > 3$ and $R_F = CF_3, C_2H_5$
$R_F R_H$ $R_H = CH_3(CH_2)_n$ with $n = 2\text{–}10$ and the types $R_F O(CH_2)_n OR_F$
$R_F O(CH_2)_n O(CH_2)_n OR_F$
$R_F(CH_2)_n O(CH_2)_n R_F$ with $R_F = CF_3$ and $CF_3(CF_2)_n$
$R_F(CH_2)_m O(CH_2)_n O(CH_2)_m R_F$ $n = 1\text{–}4$
$(CH_2)_{n(m)}$ with $n = 2\text{–}6$ and $m = 1\text{–}4$.

5 Claims, No Drawings

TREATMENT AGENT FOR OPHTHALMOLOGY AND USE THEREOF

BACKGROUND OF THE INVENTION

The invention concerns a treatment agent for ophthalmology and use thereof in ophthalmological process as for reapplying a retina, for permanent tamponade and as a vitreous humor substitute.

Liquid perfluorocarbons are suitable as a treatment liquid for reapplying a detached retina to the chorioid of the eye, by unfolding or unrolling of the retina (L. Clark, EP No 0 089 232; H. Meinert, European patent application No. 91 120184.6).

Because liquid perfluorocarbons have a suitably high density (higher than 1.6 g/cm$^3$) and an extremely low surface tension (lower than $25 \times 10^{-5}$ N/cm or 25 dyn/cm), they are suitable for unfolding or unrolling a detached retina and pressing it back into place. The low surface tension advantageously prevents the treatment liquid from passing behind the retina if it has one or more tears.

Perfluorocarbons are chemically and physiologically inert compounds, if they are in a state of high purity.

The perfluorocarbon liquids which are to be used for reapplying a detached retina must be absolutely non-toxic. Accordingly such perfluorocarbons may not contain any impurities at C-H-bonds, which by way of intramolecular HF-separation result in the formation of fluorolefinic double bonds. That means in exact terms that the perfluorocarbon liquids to be used may not contain any impurity components which also contain —CHF-groups besides —CF$_2$-groups in a molecule because that gives rise to HF-separation and linked thereon toxicity, as follows:

$$-CHF-CF_2- \rightarrow -CF=CF- + HF$$

It is also known that the perfluorocarbon liquids which are used for unfolding a detached retina, after a residence time of some days, have to be removed from the eye and substituted by another medium. That vitreous humor substitute such as for example silicone oil is used for a prolonged tamponade effect for the reason that the high density of the perfluorocarbon liquids would be against long-term tamponade (M. E. Hammer et al in: H. Mackenzie Freenam, F. I. Tolentino: PVR, Springer-Verlag 1988).

SUMMARY OF THE INVENTION

An object of the present invention is to provide a treatment agent for ophthalmology which can be used in various ways in retina treatment.

Another object of the present invention is to provide a treatment agent for ophthalmology which afford greater acceptability for a wide range of uses.

A further object of the present invention is to provide ophthalmological processes using the treatment agent.

The foregoing and other objects are attained by the invention as set forth herein.

The present invention thus provides, as new classes of compounds, modified fluorocarbons of the types $R_F(CH_2)_nR_F$
$R_FR_H$

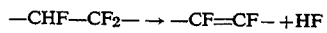

with n > 3 and $R_F$ = CF$_3$, C$_2$H$_5$
$R_H$ = CH$_3$(CH$_2$)$_n$
with n = 2–10 and the types $R_FO(CH_2)_nOR_F$
$R_FO(CH_2)_nO(CH_2)_nOR_F$
$R_F(CH_2)_nO(CH_2)_nR_F$
$R_F(CH_2)_mO(CH_2)_nO(CH_2)_mR_F$ with $R_F$ = CF$_3$ and CF$_3$(CF$_2$)$_n$
n = 1–4
(CH$_2$)$_{n(m)}$ with n = 2–6 and m = 1–4.

which are suitable both for unfolding or reapplying a retina and also for long-term tamponade and also a vitreous humor substitute in ophthalomogy.

The liquid perfluorinated compounds, or modified perfluorocarbons, are chemically and physiologically harmless and are completely non-toxic colorless liquids which are suitable for reapplying a retina, without passing behind the retina if the retina has a split therein.

The compounds used in accordance with the present invention are of a completely different structure from perfluorocarbons, being therefore compounds which only comprises carbon-fluorine bonds and which possibly have a heteroatom such as nitrogen or oxygen between the CF$_2$-groupings bearing the respective compound (briefly identified as $R_F$-groups). More specifically the compounds according to the invention comprise closed hydrocarbon-alkane groups which are bonded to perfluoroalkyl residues either directly or by way of oxygen bridges.

The compounds of the invention cannot involve any HF-separation, with the formation of fluoroelefinic double bonds, but on the contrary the closed hydrocarbon-alkane grouping also acts with a bond-enhancing effect on the C—F-bonds in the perfluoroalkyl part of the respective compound. Oxygen atoms between the $R_F$ and $R_H$-groupings also exclude intramolecular HF-separation.

Accordingly the types of compounds which can be used according to the invention, similarly to pure perfluorocarbons, are chemically and physiologically inert and thus non-toxic.

The perfluorinated compounds or types of compounds of modified perfluorocarbons, which can be used in accordance with the invention however have on the one hand the excellent properties of pure perfluorocarbons in regard to the extremely low surface tension (lower than $30 \times 10^{-5}$ N/cm or 30 dyn/cm), governed by the point that $R_F$-groups, that is to say perfluoroalkyl groups, are bonded to the molecule end, so that those compounds behave like pure perfluorocarbons.

On the other hand the densities of the modified perfluorocarbons of the invention are very substantially reduced to values of between 1.2 and 1.5 g/cm$^3$, due to the fact that those molecules contain a high proportion of hydrocarbon groups (—CH$_2$— and CH$_3$—) and possibly also oxygen bridging atoms. They therefore have substantially lower density values than pure perfluorocarbons and are suitable for long-term tamponade operations.

The modified perfluorocarbons according to the invention are therefore not only an instrument for unfolding or unrolling a retina but also for permanent tamponade. For long-term tamponade there is now no longer any need for replacement of the retina unfolding or reapplying liquid, for example a perfluorocarbon, by a liquid for long-term tamponade purposes, for example silicone oil.

The modified perfluorocarbons according to the invention are also highly suitable as a vitreous humor substitute by virtue of their chemically and physiologically inert nature, their low density relative to perfluorocarbons and their excellent surface tension, and also by virtue of their very good solubility in relation to gases, for example and preferably oxygen and carbon dioxide.

The modified perfluorocarbons according to the invention can be represented as chemically highly stable compounds by means of suitable purification processes, as high-purity and therefore completely non-toxic compounds.

In terms of their further physical properties, the modified perfluorocarbons behave as is to be expected in accordance with their respective molecular weight, that is to say their boiling point and melting point rise with increasing molecular mass while vapor pressure rises with decreasing molecular mass. That advantageously provides wide variations in respect of the liquid modified perfluorocarbons according to the invention. Similarly to pore perfluorocarbons, the modified perfluorocarbons of the invention have a high level of solubility in respect of gases, inter alia $O_2$ and $CO_2$. The modified perfluorocarbons according to the invention are scarcely soluble to not soluble in water, similarly to perfluorocarbons and hydrocarbons.

The liquid modified perfluorocarbons which are of interest in terms of ophthalmology and ophthalmological processes are colorless liquids which by virtue of their excellent chemical resistance are also highly suitable for use in relation to laser treatment (laser coagulation) because no decomposition products occur in such an operation.

The compounds according to the invention can be produced in a high state of purity to be employed in ophthalmology.

EXAMPLE

For use in ophthalmology, the modified perfluorocarbons according to the invention are firstly boiled with an acid permanganate solution. After that they are autoclaved for about 72 hours at between 150° and 180° C. with a mixture of strong aqueous potash lye (between 4 to 8 n), CaO or BaO, and a nucleophilic agent (secondary amine and/or monovalent alcohol). The autoclaved product is then separated by means of a separating funnel from the aqueous alkaline phase which possibly still contains alcohol, and the amine phase which is possibly present, successively treated a plurality of times with dilute mineral acid, $NaHCO_3$-solution, distilled water, water-free $Na_2SO_4$ and water-free $CaCl_2$, and finally subjected to fractional distillation using an efficient column.

It will be appreciated that the invention has been set forth hereinbefore solely by way of example and illustration thereof and that further modifications and alterations may be made therein without thereby departing from the spirit and scope of the invention.

What is claimed is:

1. A method of using a modified perfluorocarbon liquid compound selected from the group consisting of $R_F(CH_2)_nR_F$, $R_FR_H$, (where n>3 and $R_F=CF_3$ or $C_2F_5$ and $R_H=CH_3(CH_2)_n$, where n=2−10), $R_FO(CH_2)_nOR_F$, $R_FO(CH_2)_nO(CH_2)_nOR_F$, $R_F(CH_2)_nO(CH_2)_nR_F$ and $R_F(CH_2)_mO(CH_2)_nO(CH_2)_mR_F$ (where $R_F=CF_5$ or $CF_3(CF_2)_n$, n=1−4, and where in $(CH_2)_n$, n=2−6 and in $(CH_2)_{(m)}$, m=1−4), as a treatment agent in ophthalmology for repairing a retina.

2. A method of using a modified perfluorocarbon as set forth in claim 1 comprising a step of unfolding a retina.

3. A method of using a modified perfluorocarbon as set forth in claim 1 comprising a step of applying said agent as a tamponade for a reapplied retina.

4. A method of using a modified perfluorocarbon as set forth in claim 1 comprising a step of substituting said agent for vitreous humor in an eye.

5. A method of using a modified perfluorocarbon as set forth in claim 1 comprising laser coagulation for repairing a retina without formation of decomposition products.

* * * * *

UNITED STATES PATENT AND TRADEMARK OFFICE
CERTIFICATE OF CORRECTION

PATENT NO. : 5,441,733

DATED : August 15, 1995

INVENTOR(S) : Hasso Meinert

It is certified that error appears in the above-indentified patent and that said Letters Patent is hereby corrected as shown below:

Title page, item [30], insert--Foreign Application Priority Data:
April 1, 1992, Germany ... P 42 10 846.2
April 9, 1992, Germany ... P 42 11 958.8--.

Signed and Sealed this

Fourth Day of June, 1996

Attest:

BRUCE LEHMAN

*Attesting Officer*        *Commissioner of Patents and Trademarks*